United States Patent [19]
Lill

[11] Patent Number: 5,264,690
[45] Date of Patent: Nov. 23, 1993

[54] DEVICE FOR PROTECTING AGAINST EXCESSIVE HIGH ENERGY RADIATION HAVING A CONTROLLED LIGHT SOURCE

[75] Inventor: Ernst Lill, Müchen, Fed. Rep. of Germany

[73] Assignee: Messerschmitt-Bölkow-Blohm AG, Fed. Rep. of Germany

[21] Appl. No.: 972,777

[22] Filed: Nov. 9, 1992

[30] Foreign Application Priority Data

Nov. 7, 1991 [DE] Fed. Rep. of Germany ....... 4136588

[51] Int. Cl.$^5$ .............................................. G01J 1/20
[52] U.S. Cl. ................................ 250/201.1; 359/241; 358/229
[58] Field of Search ............................ 250/201.1, 205; 359/241, 244, 603, 601

[56] References Cited

U.S. PATENT DOCUMENTS

| | | | |
|---|---|---|---|
| 4,721,850 | 1/1988 | Sakai et al. | 250/201.1 |
| 4,920,257 | 4/1990 | Fuerthbauer et al. | 250/201.1 |
| 5,049,730 | 9/1991 | Loveland | 250/201.1 |

*Primary Examiner*—David C. Nelms
*Assistant Examiner*—Que T. Le
*Attorney, Agent, or Firm*—Evenson, McKeown, Edwards & Lenahan

[57] ABSTRACT

This invention relates to a device for the protection of eyes, electro-optical sensors and sensitive materials against high energy light beams, in which the incidence of a high energy light beam on the element to be protected is detected by a warning sensor. The warning sensor triggers a light source to provide a light beam which, with minimal delay, causes a diminution in the transmissivity of a protective element interposed in the beam path of the high intensity light beam. Due to the extremely rapid response time of these components, the protective response of the invention adapts almost immediately to changes in the intensity of an incident high energy light beam, thereby providing necessary protection and a prompt return to normal transmissivity upon termination of the potentially damaging radiation.

20 Claims, 2 Drawing Sheets

DEVICE FOR PROTECTING AGAINST EXCESSIVE HIGH ENERGY RADIATION HAVING A CONTROLLED LIGHT SOURCE

BACKGROUND AND SUMMARY OF THE INVENTION

This invention relates to a device for protecting human eyes, electro-optical sensors and sensitive materials against excessive optical power densities and energy densities.

Because of their high inherent sensitivity, eyes and electronic sensors are endangered by excessive optical power densities and energy densities. As protective measures, the state of the art provides diverse passive and active measures, such as interference filters, holographic filters, mechanical locks and self-actuating optical switches. These measures, however, frequently provide insufficient protection, either because they are effective only in a limited spectral region, or because the sensitivity of the sensor is impaired. Moreover, in some cases, after a threat posed by high energy radiation has subsided, the protective device does not revert appropriately to normal operation, or—particularly in the case of laser pulses—the reaction is too slow. Another problem of the state of the art is the high technical expenditures—mainly weight and volume—in the case of many common protective measures.

It is therefore an object of the invention to provide a protective device of the above-mentioned type which ensures reliable protection over a large spectral region with the shortest time delay, and which reacts in a coordinated manner with respect to time as well as with respect to the power densities and energy densities.

These and other objects and advantages are achieved by the protective device according to the invention, in which the incidence of a high energy light beam on the element to be protected is detected by a warning sensor. The warning sensor triggers a light source to provide a light beam which, with minimal delay, causes a diminution in the transmissivity of a protective element interposed in the beam path of the high intensity light beam. Due to the extremely rapid response time of these components, the protective response of the invention adapts almost immediately to changes in the intensity of an incident high energy light beam, thereby providing necessary protection and prompt return to normal transmissivity upon termination of the potentially damaging radiation.

The invention is thus based on the principle that the optical transmission properties of certain materials are altered by the incidence of high energy light, (preferably laser light), and that therefore their transition from a maximal absorption as well as the inverse effect can be utilized. Numerous materials exhibit such characteristics that can be utilized in this manner, of which the following are but a few examples:

Absorption of dyes,
intensity-dependent transmission action of semiconductor substances
production of plasma
self-defocussing
total internal reflection
induced scattering The decisive advantage of all these effects is their short reaction time, typically less than a nanosecond, which is absolutely necessary if they are to be used for protective purposes, particularly for protection against laser pulses. It is known that the triggering of these effects requires very high power densities in the protective medium, and to some extent a defined excitation wavelength.

In order for the interference radiation to trigger the protection of the sensor itself, the protective medium must be arranged in the focal range, which in turn, requires an additional intermediate projection. In addition, it should be noted that in prior art devices, even under these conditions, the switching and diminishing effect frequently did not occur before threshold values were reached which were above the danger limit of the used sensor. Therefore, all the protective measures of the state of the art must be considered to be unsatisfactory.

However, an optimization is achieved by utilization of the above-mentioned effects in the protective device according to the invention because they are triggered in a targeted and requirement-oriented manner by the light of an external radiation source, preferably by a laser. The power density, the wavelength and the time response of the radiation are therefore optimally adapted to the requirements by the selection of the light source, its control and by the coupling-in of its radiation energy.

Other objects, advantages and novel features of the present invention will become apparent from the following detailed description of the invention when considered in conjunction with the accompanying drawings.

DETAILED DESCRIPTION OF THE DRAWINGS

Figure 1:
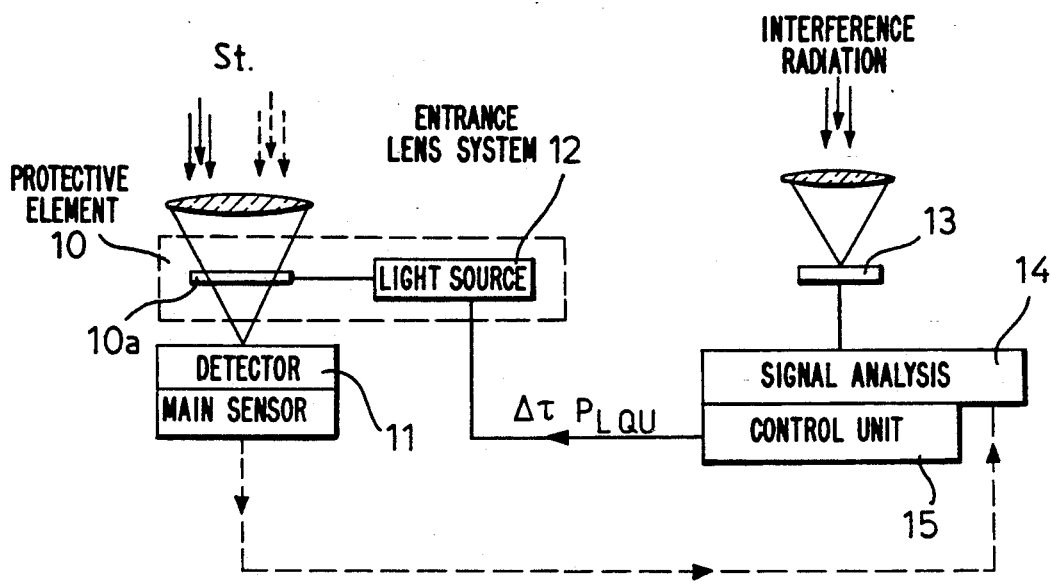
FIG. 1 is a schematic representation of an embodiment of the protective device according to the invention.

FIG. 1 is a basic representation of an embodiment of the protective apparatus according to the invention. This embodiment comprises an optical sensor 11 which is to be protected. A detector associated with the sensor 11 has a protective element 10 arranged in its beam path, and a warning sensor 13 is connected with a signal analyzing unit 14 and a control unit 15. The signal analyzing unit 14 performs a so-called threat analysis, the results of which are transmitted to the control unit 15. This control unit 15 controls and regulates the light source 12 in response to the received threat data, taking into account the pulse duration, the repetition rate and the pulse output. A microprocessor in the control unit 15 carries out the sequence control of the sensor protecting device based on the system requirements.

In the safe operating mode, the light source 12 is switched off and the transmissivity of the protecting element 10 is therefore maximal. When, however, a high energy light beam, having an excessive power density, impinges on the apparatus, it is detected by the warning sensor 13, which transmits a warning signal to the signal analysis and control unit 14. The control unit then activates the light source 12 which directs a beam of radiation on the protective element 10. The wavelength and power density of this light beam are selected so as to trigger a virtually immediate diminution of the transmissivity of the protective element 10a, to an extent which is appropriate for the interference light intensity. As the danger subsides, the control unit 15 reduces the light power coupled onto the protective element 10, so that the transmission is increased again and the sensor system 11 to be protected returns virtually without delay to its full sensitivity.

In comparison to the element to be protected—that is, the sensor 11, eye, etc.—the warning sensor 13 is designed with a considerably higher destruction threshold. However, it is also possible to provide an additional protective element, which is controlled by the same regulating loop, to protect adaptively the warning sensor. In this case, the signals of the sensor 11 to be protected may also be used for threat analysis in the signal analyzing unit 14. In a simplified version, therefore, the regulating signal for the protective element 10 (represented by the broken line in FIG. 1) may be obtained from the sensor 11 to be protected, and the warning sensor 13 will therefore not be required.

Figure 2:
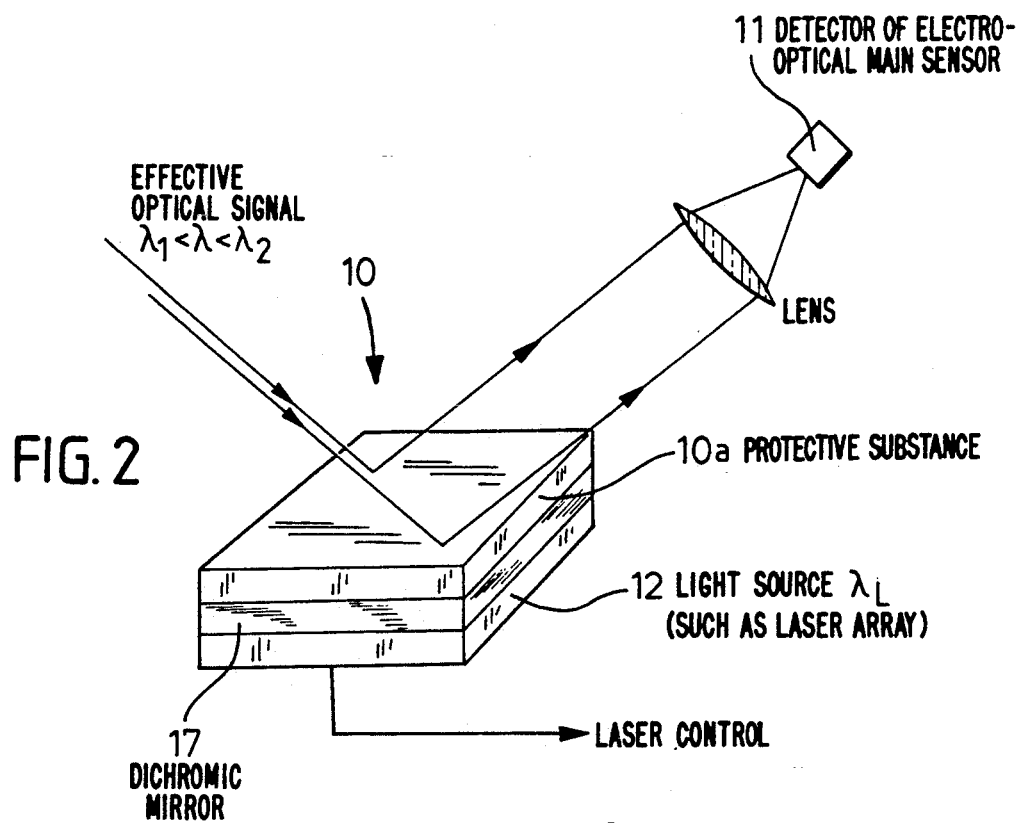
FIG. 2 is a perspective view of another embodiment of a protective device according to the invention which utilizes a mirror configuration in the case of a longitudinal coupling-in of the optical switching energy.

The coupling-in of the energy from light source 12—preferably a laser—may take place transversely as well as longitudinally, the light source 12 being arranged directly on the protective substance element 10a or feeding the energy by way of an optical waveguide 16 or an optical beam path. FIG. 2 shows an embodiment of the invention in which the optical switching energy is coupled-in longitudinally. In this embodiment, the protective element 10 is used in a so-called mirror configuration, and comprises a protective substance element 10a, a dichroic mirror 17 which is preferably equal in area and is arranged underneath, and a connected two-dimensional laser array.

In the undisturbed state, the protective substance 10a—such as a metal oxide semiconductor material—is transparent for the wavelength range of the optical effective signal. The effective signal is therefore transmitted by layer 10a and reflected on the dichroic mirror 17 in the direction of the detector 11. If the sensor is endangered, however, the light source 12 is activated (the dichroic mirror 17 being transmitting in the case of the wavelength $\lambda_L$ of the light source 12). The optical switching energy from light source 12 changes the protective substance of the element 10a into a very absorbent condition, so that the beam path to the detector 11 of the main sensor is interrupted, and the detector is therefore protected from overloading. If the light source is operated out-of-line from the protective substance element, the coupling-in of the switching energy may take place by way of optical waveguides.

Figure 3:
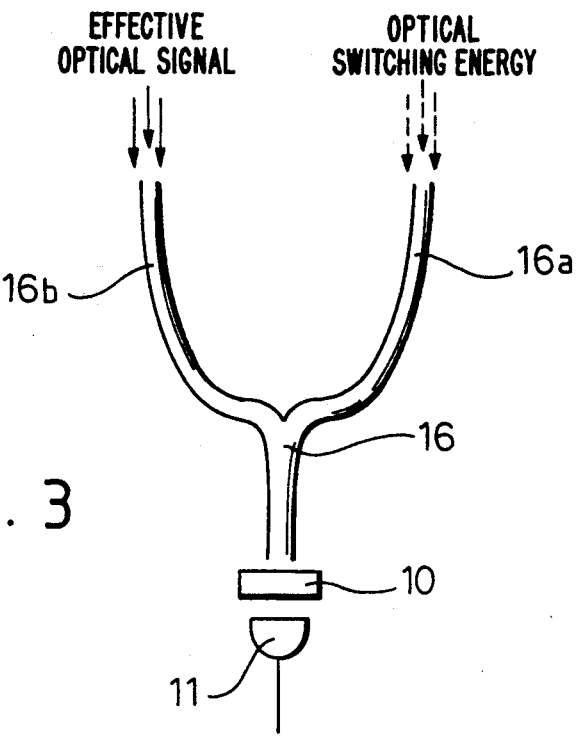
FIG. 3 is a schematic representation of a protective device according to the invention with a fiber coupling arrangement.

Another variant of the construction is shown in FIG. 3, in which the optical switching energy and the optical effective signal are superimposed by means of fiber optics 16 and are projected together on the protective element 10. This construction has the advantage that a simple superposition of the two beam portions can be carried out on a small area, so that the dimensions of the protective element may be extremely compact.

Figure 4:
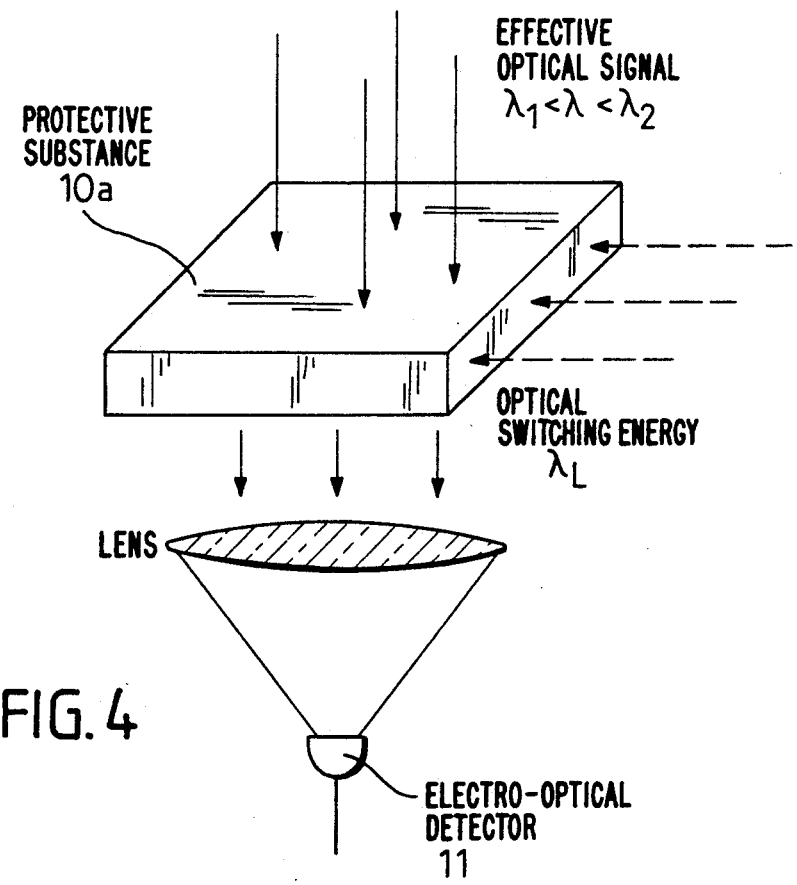
FIG. 4 is a perspective schematic diagram of a protective element for a protective device according to the invention.

FIG. 4 illustrates a transverse coupling-in of the optical switching energy into the protective element 10. In this embodiment, the element 10a is operated in transmission. In the case of transverse coupling-in, the lasers may be arranged on the edges of the protective substance element 10a. Preferably, the wavelength of the so-called switching laser or of the light source 12 is selected such that the operation of the sensor 11 is not impaired.

Other variants of the protective unit may be designed to be linear or as a two-dimensional matrix consisting of individual elements, in which case each element can be switched individually. In this case, the longitudinal coupling-in takes place by wa of a glass fiber bundle or a laser array. This can prevent partial cross-fading, should the detector of the sensor 11 consist of a one-dimensional or two-dimensional arrangement of detector elements.

Although the invention has been described and illustrated in detail, it is to be clearly understood that the same is by way of illustration and example, and is not to be taken by way of limitation. The spirit and scope of the present invention are to be limited only by the terms of the appended claims.

I claim:

1. Device for protection of sensitive elements against a light beam having excessive optical power density, comprising:
   a protective element comprising a normally light transmitting substance whose transmissivity is reduced by the incidence of light having predetermined parameters, said protective element being disposed in a beam path of the sensitive element to be protected;;
   a light source arranged to transmit light having said predetermined parameter to said protective element;
   a warning sensor arranged to receive said light beam;
   a signal analyzing unit coupled to receive an output signal from said warning sensor;
   a control unit coupled to received measurement results from said signal analysis unit to control pulse duration, repetition rate and pulse output of light transmitted by said light source.

2. A device according to claim 1, wherein the warning sensor has a high interference and destruction threshold, and has an additional protecting element assigned to it for adaptive protection, said additional protecting element being controlled by said control unit.

3. A device according to claim 1, wherein a laser is used as the light source, the energy of which is coupled into the protective substance element from a direction relative to said protective substance element which is one of transverse and longitudinal.

4. A device according to claim 1, wherein the light source is arranged directly on the protective substance element.

5. A device according to claim 2, wherein the light source is arranged directly on the protective substance element.

6. A device according to claim 3, wherein the light source is arranged directly on the protective substance element.

7. A device according to claim 1, wherein the light source inputs its energy by one of: an optical waveguide and an optical beam path.

8. A device according to claim 2, wherein the light source inputs its energy by one of: an optical waveguide and an optical beam path.

9. A device according to claim 3, wherein the light source inputs its energy by one of: an optical waveguide and an optical beam path.

10. A device according to claim 1, wherein the protective element is composed, for the longitudinal coupling-in of light, of a sandwich construction of the protective substance element, a dichroic mirror disposed underneath said protective substance, and a two-dimensional laser array underneath said dichroic mirror and used as the light source.

11. A device according to claim 4, wherein the protective element is composed, for the longitudinal coupling-in of light, of a sandwich construction of the protective substance element, a dichroic mirror disposed underneath said protective substance, and a two-dimensional laser array underneath said dichroic mirror and used as the light source.

12. A device according to claim 7, wherein the protective element is composed, for the longitudinal coupling-in of light, of a sandwich construction of the protective substance element, a dichroic mirror disposed underneath said protective substance, and a two-dimensional laser array underneath said dichroic mirror and used as the light source.

13. A device according to claim 1, wherein by means of a fiber coupling device, optical switching energy of one optical waveguide is superimposed with an optical effective signal of another optical waveguide and both are projected together on the protective element.

14. A device according to claim 1, wherein, in the case of transverse or longitudinal coupling-in of light from said light source to said protective element, optical switching energy is fed to the protective substance and the protective element is operated in transmission.

15. A device according to claim 4, wherein, in the case of transverse or longitudinal coupling-in of light from said light source to said protective element, optical switching energy is fed to the protective substance and the protective element is operated in transmission.

16. A device according to claim 7, wherein, in the case of transverse or longitudinal coupling-in of light from said light source to said protective element, optical switching energy is fed to the protective substance and the protective element is operated in transmission.

17. A device according to claim 1, wherein the protective element is constructed as a linear matrix of individual elements, wherein each element can be switched individually.

18. A device according to claim 1, wherein the protective element is constructed as a two dimensional matrix of individual elements, wherein each element can be switched individually.

19. A device according to claim 1, wherein wavelength, power and switch-on duration of the light source are adapted to interference-free function of the sensitive element to be protected.

20. A device according to claim 3, wherein wavelength, power and switch-on duration of the light source are adapted to interference-free function of the sensitive element to be protected.

* * * * *